United States Patent
Ugazio

(10) Patent No.: US 7,192,542 B2
(45) Date of Patent: Mar. 20, 2007

(54) OIL ABSORBING COMPOSITION AND PROCESS

(75) Inventor: Stephen Pierre Jean Ugazio, Cabris (FR)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 11/003,234

(22) Filed: Dec. 3, 2004

(65) Prior Publication Data

US 2005/0131143 A1 Jun. 16, 2005

(30) Foreign Application Priority Data

Dec. 15, 2003 (EP) .................................. 03293169

(51) Int. Cl.
*B01J 13/02* (2006.01)
*B01J 13/20* (2006.01)
*B32B 5/16* (2006.01)
*A61K 9/50* (2006.01)
*A61K 8/11* (2006.01)

(52) U.S. Cl. .................. 264/4; 427/213.3; 427/213.31; 427/213.33; 428/402; 428/402.2; 424/489; 424/401; 424/59; 424/70.1

(58) Field of Classification Search ................ 264/4.1, 264/4.3, 4.33, 4.7, 4; 427/213.3, 213.34, 427/213.36; 525/301, 193; 523/201; 260/835, 260/836; 428/402; 424/489, 401, 59, 70.1
See application file for complete search history.

(56) References Cited

U.S. PATENT DOCUMENTS

| | | | |
|---|---|---|---|
| 4,171,228 A * | 10/1979 | Lowrey | ...................... 106/409 |
| 4,303,679 A | 12/1981 | Raccach | |
| 4,663,068 A | 5/1987 | Hagemann et al. | |
| 5,036,109 A | 7/1991 | Chip et al. | |
| 5,102,693 A | 4/1992 | Motosugi et al. | |
| 5,137,864 A | 8/1992 | Yaguchi et al. | |
| 5,145,675 A | 9/1992 | Katz et al. | |
| 5,157,084 A | 10/1992 | Lee et al. | |
| 5,216,044 A | 6/1993 | Hoshino et al. | |
| 6,384,104 B1 * | 5/2002 | Chang et al. | ................ 523/105 |
| 2004/0121003 A1 * | 6/2004 | Chichering et al. | ......... 424/465 |
| 2005/0043458 A1 * | 2/2005 | Adamo et al. | ............... 524/379 |

FOREIGN PATENT DOCUMENTS

| | | |
|---|---|---|
| EP | 0467646 | 1/1992 |
| EP | 0545556 | 6/1993 |
| EP | 1111034 | 6/2001 |
| EP | 1027147 | 5/2002 |
| WO | WO9220742 | 11/1992 |
| WO | WO9730109 | 8/1997 |

OTHER PUBLICATIONS

Encyclopedia of Polymer Science and Technology: Microencapsulation, 2005 John Wiley & Sons, Inc. All rights reserved pp. 1 and 25.*

* cited by examiner

Primary Examiner—James J. Seidleck
Assistant Examiner—Saira B. Haider

(57) ABSTRACT

The present invention relates to a hollow sphere polymer composition suitable for absorbing active ingredients including oily substances and hydrophobic materials. A process for encapsulating one or more active ingredients using hollow sphere polymers is described.

5 Claims, No Drawings

OIL ABSORBING COMPOSITION AND PROCESS

CROSS REFERENCE TO RELATED PATENT APPLICATIONS

This is a non-provisional patent application of European patent application No. 03293169.3 filed Dec. 15, 2003.

The present invention relates to a oil absorbing compositions and a process for encapsulating oily substances and hydrophobic materials. In particular, the invention is directed to the use of hollow sphere polymers as oil absorbing compositions and a process for encapsulating active ingredients used in cosmetics.

Many active ingredients in food, cosmetics and paints are prepared as oil-in-water or water-in-oil emulsions. However, a number of these emulsions have limited stability when stored over time. Further, the activity of the active ingredients is also negatively impacted upon storage, due to deactivation, phase separation or hydrolysis. It is desirable, therefore to provide a solid carrier for active ingredients, a solid carrier that can absorb the active ingredient in an oil phase and can be readily re-dispersed to form a stable emulsion.

European Patent Publication No. EP 1 027 147 discloses the use of dried capsules prepared by coacervation to encapsulate flavors and fragrances by controlled water transport of the active ingredients into a capsule having an oil core. Unfortunately, the formulations contain low quantities of active ingredients and large amounts of water, which would negatively impact the activity of the active ingredients upon storage. There is a need for a solid carrier that is easily loaded with oily substances and hydrophobic materials that incorporate one or more active ingredients.

Inventors have discovered that hollow sphere polymers can effective absorb one or more active ingredients, including oily substances and hydrophobic materials, and encapsulate the one or more active ingredients to form flowable powders that are non-dusting. The hollow sphere polymers when combined with one or more active ingredients, including oily substances and hydrophobic materials, are milled to encapsulate the active ingredients, a process that does not require spray drying, which could degrade or deactivate the active ingredients. The flowable non dusting powder produced is easily re-dispersed in aqueous solutions to form stable emulsions and is also readily processed by compaction into tablets. Moreover, the density of the hollow spheres polymer used to encapsulate the active ingredients, including oily substances and hydrophobic materials, is low and provides floating tablets when the encapsulated powders are compacted.

Accordingly, the invention provides a process for encapsulating one or more active ingredients comprising the steps of: (a) milling one or more hollow sphere polymers; and (b) contacting the milled polymers with one or more active ingredients, including oily substances and hydrophobic materials.

Moreover, the invention provides a process for preparing flowable, dry polymer solids having reduced dusting comprising: (a) milling one or more hollow sphere polymers; and (b) contacting the milled polymers with one or more active ingredients, including oily substances and hydrophobic materials.

Polymers usefully employed in accordance with the invention are hollow sphere polymers. According to an exemplary embodiment, the polymers are prepared from aqueous emulsion polymers. Suitable polymers include, but are not limited to, latex polymer particles. Latex particles useful in the method of this invention are latex particles that include voids and that are formed from a multi-staged particle comprising at least one core polymer and at least one shell polymer. The core polymer and shell polymer may be made in a single polymerization step or in a sequence of polymerization steps. Latex particles that include voids are also referred to as hollow sphere latex particles. Latex particles that include voids are also referred to as core shell latex polymers, wherein the core polymer is swellable with at least one swelling agent (also referred to as swellant) including solvents, water and aqueous bases, is swollen with at least one swelling agent, wherein the core is a void comprising water and wherein the void comprises at least one swelling agent. For the purposes of the present invention, the terms, "sheath" and "shell" are considered synonymous and refer to the total shell polymer composition (not including the core portion) prepared from single or multi-stage polymerizations. The emulsion polymers are prepared as dispersions, typically as aqueous dispersion.

According to one embodiment, suitable polymers include latex polymer particles having selected cross-linker levels used in a shell portion of the latex polymer particles that are based on: (1) monomeric compositions containing polyethylenically unsaturated monomers, (2) monomeric compositions containing multifunctional monomers having at least one functional group capable of vinyl copolymerization and at least one functional group capable of reaction with suitable reactive molecules to produce post-polymerization cross-linking, and (3) combinations thereof. The specific emulsion polymers include latex polymer particles containing a void and having a particle size from 20 to 1000 nanometers. The latex polymer particles comprise a shell portion prepared, as described in U.S. Pat. No. 6,384,104, by one or more steps selected from: (i) polymerization to incorporate from 4 to 80 percent monomeric units, based on total weight of the shell portion, of one or more polyethylenically unsaturated monomers; and (ii) polymerization to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization cross-linking.

The latex polymer particles usefully employed in the invention have a particle size from 20 to 1000 nanometers (nm) (or 0.02 to 1 micron, µm), including particles sizes from 100 to 600 nm (0.1 to 0.6 µm), from 200 to 500 nm (0.2 to 0.5 µm), and from 300 to 400 nm (0.3 to 0.4 µm), as measured by a Brookhaven BI-90 photon correlation spectrometer.

For a given particle size, it is desirable to produce latex polymer particles with a maximum void fraction as current processing techniques and particle integrity will permit. Typically, the latex polymer particles contain a void or voids with a void fraction from 0.01 to 0.70, including void fractions from 0.05 to 0.50, from 0.10 to 0.40, and from 0.20 to 0.35. The void fractions are determined by comparing the volume occupied by the latex polymer particles after they have been compacted from a dilute dispersion in a centrifuge to the volume of non-voided particles of the same composition. Void fraction can also be expressed as a percentage (%).

The latex polymer particles useful in the invention are prepared by conventional polymerization techniques including sequential emulsion polymerization. Dispersions of the latex polymer particles are prepared according to processes including those disclosed in U.S. Pat. Nos. 4,427,836; 4,469,825; 4,594,363; 4,677,003; 4,920,160; and 4,970,241. The latex polymer particles may also be prepared, for example, by polymerization techniques disclosed in European Patent Applications EP 0 267 726; EP 0 331 421; EP 0 915 108 and U.S. Pat. Nos. 4,910,229; 5,157,084; 5,663,213 and 6,384,104.

In a separate embodiment, other emulsion polymer dispersions useful in the invention include heteropolymer dispersions, bimodal dispersions and dispersions prepared from water insoluble monomers. These latex polymer particles are prepared according to processes including those disclosed in U.S. Pat. Nos. 4,456,726, 4,468,498, 4,539,361, 5,521,266, 5,340,858, 5,350,787 or 5,352,720. The latex polymer particles may also be prepared, for example, by polymerization techniques disclosed in European Patent Applications EP 0 265 142, EP 0 119 054 and EP 0 118 325, EP 0 022 663 or EP 0 342 944.

In a separate embodiment, other latex particles useful in the invention are latex particles including minute void particles and layers that are expanded by expansion of a gas or a low boiling solvent in a foaming process, for example, that are disclosed in U.S. Pat. Nos. 5,102,693 and 5,137,864. This includes penetration of the shell polymer into the core polymer. Penetration of the shell polymer into the core polymer may be controlled by both thermodynamic and kinetic factors. Thermodynamic factors may determine the stability of the ultimate particle morphology according to the minimum surface free energy change principle. However, kinetic factors such as the viscosity of the core polymer at the polymerization temperature of the shell and the swelling time afforded the second stage polymer may modify the final degree of penetration. Thus, various process factors may control penetration of the shell into the core, and ultimately the morphology of the void structure in the expanded and dried particle. Such processes are known in the emulsion polymerization art such as, for example, in U.S. Pat. Nos. 5,036,109; 5,157,084; and 5,216,044. The glass transition temperature of the shell polymer is typically greater than 40° C. as calculated using the Fox equation; the particles may be cross-linked and may have functionalized surfaces.

Also contemplated are multi-modal particle size emulsion polymers wherein two or more distinct particle sizes or very broad distributions are provided as is taught in U.S. Pat. Nos. 5,340,858; 5,350,787; 5,352,720; 4,539,361; and 4,456,726.

As used herein, the term "sequentially emulsion polymerized" or "sequentially emulsion produced" refers to polymers (including homopolymers and copolymers) which are prepared in aqueous medium by an emulsion polymerization process in the presence of the dispersed polymer particles of a previously formed emulsion polymer such that the previously formed emulsion polymers are increased in size by deposition thereon of emulsion polymerized product of one or more successive monomer charges introduced into the medium containing the dispersed particles of the pre-formed emulsion polymer.

In the sequential emulsion polymerization of a multi-stage emulsion polymer, the term "seed" polymer is used to refer to an aqueous emulsion polymer dispersion which may be the initially-formed dispersion, that is, the product of a single stage of emulsion polymerization or it may be the emulsion polymer dispersion obtained at the end of any subsequent stage except the final stage of the sequential polymerization.

The glass transition temperature ("Tg") of the emulsion polymers used herein are those calculated by using the Fox equation (T. G. Fox, Bull. Am. Physics Soc., Volume 1, Issue No. 3, page 123(1956)). that is, for calculating the Tg of a copolymer of monomers M1 and M2, $$1/Tg(\text{calc.}) = w(M1)/Tg(M1) + w(M2)/Tg(M2)$$

wherein

Tg(calc.) is the glass transition temperature calculated for the copolymer w(M1) is the weight fraction of monomer M1 in the copolymer w(M2) is the weight fraction of monomer M2 in the copolymer Tg(M1) is the glass transition temperature of the homopolymer of M1

Tg(M2) is the glass transition temperature of the homopolymer of M2, all temperatures being in ° K.

The glass transition temperatures of homopolymers may be found, for example, in "Polymer Handbook", edited by J. Brandrup and E. H. Immergut, Interscience Publishers.

According to one embodiment, latex polymer particles useful in the method of this invention are formed from a multi-staged particle comprising at least one core polymer and at least one shell polymer. The core polymer and shell polymers may each be made in a single polymerization step or in a sequence of polymerization steps. While the core may be made in single stage (or step) of the sequential polymerization and the shell may be the product of a single sequential step following the core stage, preparation of the core component may involve a plurality of steps in sequence followed by preparation of the shell, which may also involve a series of sequential steps. The amount of polymer deposited to form the shell portion or shell polymer is generally such as to provide an overall size of the finished multistage polymer particle of between 0.05 to 1 micron. The ratio of the core weight to the total polymer particle weight is from $\frac{1}{4}$ (25 wt. % core) to $\frac{1}{100}$ (1 wt. % core) and includes a ratio from $\frac{1}{8}$ (12 wt. % core) to $\frac{1}{50}$ (2 wt. % core).

The monomers used in the emulsion polymerization of the "core" (or "seed") polymer of the latex polymer particles preferably include at least 5 weight % of one or more monoethylenically unsaturated monomers containing at least one carboxylic acid group, based on total monomer weight of the core. The core polymer may be obtained, for example, by the emulsion homopolymerization of the monoethylenically unsaturated monomer containing at least one carboxylic acid group or by copolymerization of two or more of the monoethylenically unsaturated monomers containing at least one carboxylic acid group. Preferably, the monoethylenically unsaturated monomer containing at least one carboxylic acid group is co-polymerized with one or more non-ionic (that is, having no ionizable group) ethylenically unsaturated monomers. The presence of the ionizable acid group makes the core swellable by the action of a swelling agent, such as an aqueous or gaseous medium containing a base to partially neutralize the acid core polymer and cause swelling by hydration.

As used herein, the term "(meth)acrylic" refers to either the corresponding acrylic or methacrylic acid and derivatives; similarly, the term "alkyl (meth)acrylate" refers to either the corresponding acrylate or methacrylate ester. As used herein, all percentages referred to will be expressed in weight percent (%), based on total weight of polymer or composition involved, unless specified otherwise.

Typically, emulsion polymers of the invention are water insoluble and are dispersible in water. As used herein, the term "water soluble", as applied to monomers, indicates that the monomer has a solubility of at least 1 gram per 100 grams of water, preferably at least 10 grams per 100 grams of water and more preferably at least about 50 grams per 100 grams of water. The term "water insoluble", as applied to monomers, refers to monoethylenically unsaturated monomers which have low or very low water solubility under the conditions of emulsion polymerization, as described in U.S. Pat. No. 5,521,266. An aqueous system refers to any solution containing water.

The core polymer may optionally contain from 1 to 20 wt. %, including from 2 to 10%, based on the total monomer weight of the core, of polyethylenically unsaturated monomer units, such as, for example, ethylene glycol di(meth)acrylate, allyl (meth)acrylate, 1,3-butanediol di(meth)acrylate, diethylene glycol di(meth)acrylate, trimethylolpropane tri(meth)acrylate and divinylbenzene. Alternatively, the core polymer may optionally contain from 0.1 to 60 wt. %, based on the total monomer weight of the core, of butadiene.

Suitable monoethylenically unsaturated monomers containing at least one carboxylic acid group useful in preparation of the "core" polymer, include, for example, acrylic acid, methacrylic acid, acryloxypropionic acid, (meth)acryloxypropionic acid, itaconic acid, aconitic acid, maleic acid or anhydride, fumaric acid, crotonic acid, monomethyl maleate, monomethyl fumarate and monomethyl itaconate. In one embodiment, the carboxylic acid group containing monomer is acrylic acid.

Suitable non-ionic ethylenically unsaturated monomers useful in preparation of the "core" polymer, include, for example, styrene, vinyltoluene, ethylene, vinyl acetate, vinyl chloride, vinylidene chloride, acrylonitrile, (meth)acrylamide, ($C_1$–$C_{22}$)alkyl and ($C_3$–$C_{20}$)alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate and stearyl (meth)acrylate.

The monomers used in the emulsion polymerization of the "shell" (or "sheath") polymer of the latex polymer particles preferably comprise one or more non-ionic ethylenically unsaturated monomers. Optionally, one or more monoethylenically unsaturated monomers containing at least one carboxylic acid group may be polymerized in the shell, such as, for example, acrylic acid, methacrylic acid, acryloxypropionic acid, methacryloxypropionic acid, aconitic acid, crotonic acid, maleic acid (and derivatives such as corresponding anhydride, amides and esters), fumaric acid (and derivatives such as corresponding amides and esters), itaconic and citraconic acids (and derivatives such as corresponding anhydrides, amides and esters). Acrylic acid and methacrylic acid are preferred carboxylic acid group-containing monomers. When present in the shell polymer, the amount of carboxylic acid group-containing monomer units is from 0.1 to 10%, including from 0.5 to 5%, based on total weight of the shell portion of the polymer particle.

Optionally, one or more monoethylenically unsaturated monomers containing at least one "non-carboxylic" acid group may be polymerized in the shell, such as, for example, allylsulfonic acid, allylphosphonic acid, allyloxybenzenesulfonic acid, 2-acrylamido-2-methylpropanesulfonic acid (the acryonym "AMPS" for this monomer is a trademark of Lubrizol Corporation, Wickliffe, Ohio, USA), 2-hydroxy-3-(2-propenyloxy)propanesulfonic acid, 2-methyl-2-propene-1-sulfonic acid, 2-methacrylamido-2-methyl-1-propane-sulfonic acid, 3-methacrylamido-2-hydroxy-1-propanesulfonic acid, 3-sulfopropyl acrylate, 3-sulfopropyl methacrylate, isopropenylphosphonic acid, vinyl-phosphonic acid, phosphoethyl methacrylate, styrenesulfonic acid, vinylsulfonic acid and the alkali metal and ammonium salts thereof.

Preferred unsaturated "non-carboxylic" acid monomers are 2-acrylamido-2-methyl-propanesulfonic acid and styrenesulfonic acid. When present in the shell polymer, the amount of unsaturated "non-carboxylic" acid monomer units is from 0.5 to 10%, including from 1 to 5%, based on total weight of the shell portion of the polymer particle.

Suitable non-ionic ethylenically unsaturated monomers useful in preparing the shell polymer include, for example, vinyl acetate, acrylonitrile, methacrylonitrile, nitrogen-containing ring compound unsaturated monomers, vinylaromatic monomers, ethylenic monomers and selected (meth)acrylic acid derivatives. In one embodiment of the invention, the shell portion of the latex polymer particles comprises as polymerized units from zero to 95% (meth)acrylic acid derivative monomer and from zero to 80% vinylaromatic monomer, based on total weight of the shell portion.

In one embodiment, one class of (meth)acrylic acid derivative is represented by ($C_1$–$C_{22}$)alkyl (meth)acrylate, substituted (meth)acrylate and substituted (meth)acrylamide monomers. Each of the monomers can be a single monomer or a mixture having different numbers of carbon atoms in the alkyl portion. Preferably, the monomers are selected from one or more of ($C_1$–$C_4$)alkyl (meth)acrylates, hydroxy ($C_2$–$C_4$)alkyl (meth)acrylates (such as hydroxyethyl methacrylate and hydroxypropyl methacrylate), dialkylamino ($C_2$–$C_4$)alkyl (meth)acrylates (such as dimethylaminoethyl methacrylate) and dialkylamino($C_2$–$C_4$)alkyl (meth)acrylamides (such as dimethylaminopropyl methacrylamide). The alkyl portion of each monomer can be linear or branched.

Suitable examples of alkyl (meth)acrylate monomers where the alkyl group contains 1 to 4 carbon atoms include methyl methacrylate (MMA), methyl and ethyl acrylate, propyl methacrylate, butyl methacrylate (BMA), butyl acrylate (BA), isobutyl methacrylate (IBMA) and combinations thereof.

Suitable examples of alkyl (meth)acrylate monomers where the alkyl group contains 10 or more carbon atoms include decyl methacrylate, isodecyl methacrylate, dodecyl methacrylate (also known as lauryl methacrylate), tetradecyl methacrylate (also known as myristyl methacrylate), pentadecyl methacrylate, hexadecyl methacrylate (also known as cetyl methacrylate), octadecyl methacrylate (also known as stearyl methacrylate), eicosyl methacrylate, behenyl methacrylate and combinations thereof.

In one embodiment, the shell portion of the latex polymer particles comprises, as polymerized units, from 5 to 95%, including from 10 to 80% and from 20 to 70%, based on total weight of the shell portion, of (meth)acrylic acid derivative monomer selected from one or more of methyl acrylate, methyl methacrylate, ethyl acrylate, ethyl methacrylate, butyl acrylate, butyl methacrylate, isobutyl acrylate, isobutyl methacrylate, hydroxyethyl methacrylate, hydroxypropyl methacrylate, dimethylaminoethyl methacrylate and dimethylaminopropyl methacrylamide.

Suitable vinylaromatic monomers include, for example, styrene, α-methylstyrene, vinyltoluene, alkyl-substitituedstyrene (such as t-butylstyrene and ethylvinylbenzene), halogenated styrenes (such as chlorostyrene and 3,5-bis (trifluoromethyl)styrene); styrene, ethylvinylbenzene and t-butylstyrene are preferred vinylaromatic monomers. When present in the shell polymer, the amount of vinylaromatic monomer units is from 1 to 80%, including amounts of vinylaromatic monomer units from 5 to 70% and from 10 to 50%, based on total weight of the shell portion of the polymer particle.

Suitable examples of nitrogen-containing unsaturated ring compound monomers include vinylpyridine, 2-methyl-5- vinylpyridine, 2-ethyl-5-vinylpyridine, 3-methyl-5-vinylpyridine, 2,3-dimethyl-5-vinylpyridine, 2-methyl-3-ethyl-5-vinylpyridine, methyl-substituted quinolines and isoquinolines, 1-vinylimidazole, 2-methyl-1-vinylimidazole, N-vinylcaprolactam, N-vinylbutyrolactam and N-vinylpyrrolidone.

Additional suitable monomers include ethylenic monomers (for example, ethylene, propylene, isobutylene, long chain alkyl α-olefins (such as ($C_{10}$–$C_{20}$)alkyl α-olefins), vinyl halides (such as vinyl chloride, vinyl fluoride, vinyl bromide), vinylidene halides (such as vinylidene chloride and vinylidene fluoride), partially halogenated (meth)acrylates (such as 2-(perfluoro-dodecyl)ethyl acrylate, 2-(perfluorododecyl)ethyl methacrylate, 2-(perfluoro-hexyl)ethyl acrylate, 2-(perfluorohexyl)ethyl methacrylate, hexafluoroisopropyl methacrylate, 2,2,3,3-tetrafluoropropyl acrylate and 2,2,2-trifluoroethyl methacrylate), and partially halogenated alkenes (such as 1,1,1-trifluoro-2,2-(trifluoromethyl)-butene).

The glass transition temperature ($T_g$) of emulsion polymers usefully employed in accordance with the invention are of a wide range and will vary according to the polymer morphology (e.g core shell, multi-stage) of a particular emulsion polymer.

According to one embodiment of the invention, monomers that comprise the shell are selected to provide a $T_g$ in at least one shell which is high enough to support the void within the latex particle. Preferably the $T_g$ of at least one shell is greater than 50° C., more preferably greater than 60° C. and most preferably greater than 70° C., as measured by differential scanning calorimetry (DSC).

When the shell portion of the latex polymer particle is provided by a single stage polymerization process upon the core polymer, the entire shell portion produced may be referred to as the sheath, shell or "outermost" shell. However, when the shell portion is provided by a multi-stage polymerization process, then the "outermost" shell is defined by the composition of the final distinct polymerization stage used to prepare the latex particles. Typically, the "outermost" shell, when provided by a multistage polymerization process, will comprise at least about 25%, preferably at least 50% and more preferably at least 75% of the total shell portion of the latex polymer particle. Preferably, the cross-linking levels used to achieve the beneficial effects of the present invention are incorporated predominantly into the "outermost" shell of the latex particles. Cross-linking levels, unless indicated otherwise, are based on the total shell portion of the latex polymer particle, regardless of the number of stages used to prepare the latex particles.

The void of the latex polymer particles is preferably produced by swelling the acid core with an aqueous basic swellant that permeates the shell and expands the core. This expansion may involve partial merging of the outer periphery of the core into the pores of the inner periphery of the shell and also partial enlargement or bulging of the shell and the entire particle overall. When the swellant is removed by drying, the shrinkage of the core develops a microvoid, the extent of which depends on the resistance of the shell to restoration to its previous size. Suitable swelling agents for the core include, for example, ammonia, ammonium hydroxide, alkali metal hydroxides' (such as sodium hydroxide), and volatile lower aliphatic amines (such as trimethylamine and triethylamine). The swelling step may occur during any of the multi-stage shell polymerization steps, between any of the staged polymerization steps, or at the end of the multi-stage polymerization process.

Cross-linking of the shell portion of the latex particles is required to achieve enhanced storage stability of UV radiation-absorption compositions. The cross-linking level is from 4 to 80%, including cross-linking levels from 5 to 70%, from 10 to 60% and from 20 to 50%, based on total weight of the shell polymer portion of the latex particles. For latex particles based on multi-stage polymerization, it is preferable that the cross-linking take place predominantly in the "outermost" shell of the latex particle; typically, the cross-linking level is from 10 to 100%, including cross-linking levels from 15 to 70% and from 20 to 60%, based on weight of the "outermost" shell polymer portion of the latex particles, where the cross-linking is based on polymerized monomer units of one or more polyethylenically unsaturated monomers and multifunctional monomers. At total shell cross-linking levels below 4%, the cross-linking level is not sufficient to provide satisfactory SPF Enhancement Retention of formulated personal care formulations containing the latex particles.

Cross-linking in the shell can be derived from the use of one or more of the polyethylenically unsaturated monomers. Suitable polyethylenically unsaturated cross-linkers include, for example, di(meth)acrylates, tri(meth)acrylates, tetra(meth)acrylates, polyallylic monomers, polyvinylic monomers and (meth)acrylic monomers having mixed ethylenic functionality.

Di(meth)acrylates cross-linkers useful in the present invention include, for example, bis(1-acryloxy-2-hydroxypropyl)phthalate, bis(1-methacryloxy-2-hydroxypropyl)-phthalate, bis(2-acryloxyethyl)phosphate, bis(2-methacryloxyethyl)phosphate, bis(acryloxy-2-hydroxypropyloxy) diethylene glycol, bis(methacryloxy-2-hydroxy-propyloxy) diethylene glycol, bisphenol A diacrylate, bisphenol A dimethacrylate, bisphenol A di-(3-acryloxyethyl)ether, bisphenol A di-(3-methacryloxyethyl)ether, bisphenol A di-(3-acryloxy-2-hydroxypropyl)ether, bisphenol A di-(3-methacryloxy-2-hydroxypropyl)ether, 1,3-butanediol diacrylate, 1,3-butanediol dimethacrylate, 1,4-butanediol di-(3-acryloxy-2-hydroxypropyl)ether, 1,4-butanecdiol di-(3-methacryloxy-2-hydroxypropyl)ether, 1,4-butanediol diacrylate, 1,4-butanediol dimethacrylate, 1,3-butanediol bis (acryloxypropionate), 1,3-butanediol bis(methacryloxypropionate), 1,4-butanediol bis(acryloxypropionate), 1,4-butanediol bis(methacryloxypropionate), 2-butene-1,4-diol diacrylate, 2-butene-1,4-diol dimethacrylate, 1,4-cyclohexanediol diacrylate, 1,4-cyclo-hexanediol dimethacrylate, 1,10-decanediol diacrylate, 1,10-decanediol dimethacrylate, diethylene glycol diacrylate, diethylene glycol dimethacrylate, 2,2-dimethyl-1,3-propanediol diacrylate, 2,2-dimethyl-1,3-propanediol dimeth-acrylate, dipentaerythritol ether acrylate, dipentaerythritol ether methacrylate, diphenolic acid di-(3-acryloxy-2-hydroxypropyl)ether, diphenolic acid di-(3-methacryloxy-2-hydroxypropyl)ether, dipropylene glycol diacrylate, dipropylene glycol dimethacrylate, 7,7,9-trimethyl-3,13-dioxo-3,14-dioxa-5,12-diazahexa-decane-1, 16-diol diacrylate, 7,7,9-trimethyl-3,13-dioxo-3,14-dioxa-5, 12-diaza-hexadecane-1,16-diol dimethacrylate, 1,12-dodecanediol diacrylate, 1,12-dodec-anediol dimethacrylate, 1,2-ethanediol diacrylate, 1,2-ethanediol dimethacrylate, 1,2-ethanediol bis(acryloxypropionate), 1,2-ethanediol bis(methacryloxy-propionate), 1,6-hexanediol diacrylate, 1,6-hexanediol dimethacrylate, 1,9-nonanediol diacrylate, 1,9-nonanediol dimethacrylate, 1,5-pentanediol diacrylate, 1,5-pentanediol dimethacrylate, 1,4-phenylenediacrylate, 1,4-phenyl-enedimethacrylate, 1-phenyl-1,2-ethanediol diacrylate, 1-phenyl-1,2-ethanediol dimethacrylate, polyoxyethyl-2,2-di(p-hydroxyphenyl)propane diacrylate, polyoxyethyl-2,2-di(p-hydroxyphenyl)propane dimethacrylate, 1,2-propanediol diacrylate, 1,2-propanediol dimethacrylate, 1,3-propanediol diacrylate, 1,3-propanediol dimethacrylate, propoxylated bisphenol A diacrylate, propoxylated bisphenol A dimethacrylate, tetrabromobisphenol A di-(3-acryloxy-2-hydroxy-propyl)ether, tetrabromobisphenol A di-(3-methacryloxy-2-hydroxypropyl)ether, tetrachlorobisphenol A di-(3-acryloxy-2-hydroxypropyl)ether, tetrachloro-bisphenol A di-(3-methacryloxy-2-hydroxypropyl)ether, tetraethylene glycol diacrylate, tetraethylene glycol dimethacrylate, triethylene glycol diacrylate, triethylene glycol dimethacrylate, 2,2,4-trimethyl-1,3-pentanediol diacrylate, 2,2,4-trimethyl-1,3-pentanediol dimethacrylate, tripropylene glycol diacrylate, and tripropylene glycol dimethacrylate. Additional suitable di(methacrylates) cross-linkers include, for example, aromatic fluorinated diacrylates (see U.S. Pat. No. 5,380,901 for further general and specific details), fluorinated diacrylates having structure 1,3-[CH$_2$=CHCO$_2$CH$_2$CHOHCH$_2$OC(CF$_3$)$_2$]$_2$-C$_6$H$_3$R$_f$ where R$_f$=C$_1$–C$_{30}$ (see U.S. Pat. No. 4,914,171 for further general and specific details), fluorinated diacrylates (see European Patent Application EP 0 529 895 for further general and specific details), 1,3-bis(2-hydroxyhexafluoro-2-propyl)benzene diacrylate, 1,3-bis(2-hydroxyhexafluoro-2-propyl)benzene dimethacrylate, 1,3-bis(hydroxyperfluoroalkyl)benzene diacrylates and trifluoromethyl analogs of bisphenol A (meth)acrylates.

Tri(meth)acrylates cross-linkers useful in the present invention include, for example, 1,2,4-butanetriol triacrylate, 1,2,4-butanetriol trimethacrylate, glycerol tri-acrylate, glycerol trimethacrylate, pentaerythritol triacrylate, pentaerythritol trimethacrylate, polyoxypropyltrimethylolpropane triacrylate, polyoxypropyl-trimethylolpropane trimethacrylate, silicone triacrylate, silicone trimeth-acrylate, 1,3,5-triacryloylhexahydro-s-triazine, 1,3,5-trimethacryloylhexahydro-s-triazine, trimethylolethane triacrylate, trimethylolethane trimethacrylate, 1,1,1-trimethylol propane triacrylate, 1,1,1-trimethylol propane trimethacrylate, 1,2,3-trimethylol propane triacrylate, 1,2,3-trimethylol propane trimethacrylate, 1,1,1-trimethylol propane tris(acryloxypropionate), 1,1,1-trimethylol propane tris(methacryloxypropionate), 1,2,3-trimethylol propane tris(acryloxypropionate), 1,2,3-trimethylol propane tris(methacryloxypropionate), tris-(2-acryloxyethyl)isocyanurate, tris-(2-methacryloxyethyl) isocyanurate.

Tetra(meth)acrylates cross-linkers useful in the present invention include, for example, pentaerythritol tetraacrylate, pentaerythritol tetramethacrylate, pentaerythritol tetrakis (acryloxypropionate), pentaerythritol tetrakis(methacryloxypropionate).

Polyallylic monomers useful as cross-linkers in the present invention include, for example, diallyl carbonate, diallyl fumarate, diallyl glutarate, diallyl itaconate, diallyl maleate, diallyl phthalate, diallyl succinate, diisopropenylbenzene, triallyl cyanurate, triallyl isocyanurate, triallyl phosphate, and 1,3,5-triisopropenyl-benzene.

Polyvinylic monomers useful as cross-linkers in the present invention include, for example, diethyleneglycol divinyl ether, divinylbenzene, divinyl ketone, divinylpyridine, divinyl sulfide, divinyl sulfone, divinyltoluene, divinylxylene, glycerol trivinyl ether, trivinylbenzene, and 1,2,4-trivinylcyclohexane, N,N'-methylenebisacrylamide, partially fluorinated α,ω-dienes such as CF$_2$=CFCF$_2$CF$_2$CH$_2$CH=CH$_2$ (see PCT Patent Application WO 96/10047 for further general and specific details), trifluoroalkadienes (see U.S. Pat. No. 5,043,490 for further general and specific details), trifluorodivinylbenzenes (see U.S. Pat. No. 5,043,490 for further general and specific details) and fluorinated divinyl ethers of fluorinated 1,2-ethanediol (see U.S. Pat. No. 5,589,557 for further general and specific details). In one embodiment, the polyvinylic monomer is divinylbenzene.

(Meth)acrylic monomers having mixed ethylenic functionalty that are useful as cross-linkers in the present invention include, for example, the acrylate ester of neopentyl glycol monodicyclopentenyl ether, allyl acryloxypropionate, allyl acrylate, allyl methacrylate, crotyl acrylate, crotyl methacrylate, 3-cyclohexenylmethyleneoxyethyl acrylate, 3-cyclohexenylmethyleneoxyethyl methacrylate, dicyclopentadienyloxyethyl acrylate, dicyclopentadienyloxyethyl methacrylate, dicyclopentenyl acrylate, dicyclopentenyl methacrylate, dicyclopentenyloxyethyl acrylate, dicycolpentenyloxyethyl methacrylate, methacrylate ester of neopentyl glycol monodicyclopentenyl ether, methallyl acrylate, trimethylolpropane diallyl ether mono-acrylate, trimethylolpropane diallyl ether mono-methacrylate and N-allyl acrylamide. In one embodiment, the (meth)acrylic monomer having mixed ethylenic functionalty is allyl methacrylate.

Another route useful to cross-link the shell portion of the latex polymers is based on the use of one or more multifunctional monomers (MFM) to provide post-polymerization cross-linking and reinforcement of the sheath. The MFM comprise at least one functional group capable of vinyl copolymerization and at least one functional group capable of reaction with suitable reactive molecules. Suitable functional groups and reactive molecules for post-polymerization cross-linking of the polymer sheath include, for example, reacting polyol functional groups in the sheath with acid and aldehyde (such as formaldehyde) reactive molecules; reacting siloxane functional groups in the sheath with primary amine or amide reactive molecules; the addition of Zn (II) to poly(acid) functional groups in the sheath; irradiation; heat curing of functional groups in sheath with or without additional initiator; and the addition of anhydride, isocyanate, epoxysiloxane, diepoxide (such as bisphenol A diglycidyl ether) and hydroxy acid reactive molecules to amine, alcohol and carboxyl/(ate) functional groups which make up the sheath matrix.

Multifunctional monomers (MFM) suitable for post-polymerization cross-linking include, for example, vinylsiloxanes, acryloylsiloxane, methacryloylsiloxanes, acetoacetoxyalkyl (meth)acrylates (such as acetoacetoxyethyl methacrylate or AAEM), N-alkylol (meth)acrylamides, epoxy (meth)acrylates (such as glycidyl methacrylate), acryloylisocyanates and methacryloylisocyanates. Suitable vinylsiloxanes include, for example, vinyltrimethoxysilane, vinyltriethoxysilane, vinytrioxy-propylsilane, acrylamidopropyltrimethoxysilanes, methacrylamidopropyltri-methoxysilanes, styrylethyltrimethoxysilane and monomers known as Silquest™ silanes (Whitco Corp., Tarrytwon, N.Y., USA). Suitable acryloylsiloxanes and methacryloylsilanes include, for example, 3-acryloxypropyltrimethoxysilane, methacryloxypropyltrimethoxysilane, (3-acryloxypropyl)methyldialkoxysilanes and Silquest™ silanes. Suitable N-alkylol (meth)acrylamides include, for example, N-methylol acrylamide, N-methylol methacrylamide, N-butoxymethyl acrylamide, isobutoxymethyl acrylamide and methyl acrylamidoglycolate methyl ether. In one embodiment, the MFM is selected from acetoacetoxyethyl methacrylate, N-methylol methacrylamide and glycidyl methacrylate.

A shell polymer based on MFM as described above may be reacted with reactive molecules selected from amines, diamines, amino acids and aminoalkyltrialkoxysilanes; optionally followed by the addition of other reactive molecules: aldehydes (such as formaldehyde), dialdehydes (such as glutaric dialdehyde), hydrazides and dihydrazides (such as succinic dihydrazide) to form post-polymerization cross-linked sol-gels.

In one embodiment, the emulsion polymers are latex polymer particles containing a void and having a particle size from 20 to 1000 nanometers. The latex polymer particles comprise a shell portion prepared, as described in U.S. Pat. No. 6,384,104, by one or more steps selected from: (i) polymerization to incorporate from 4 to 80 percent monomeric units, based on total weight of the shell portion, of one or more polyethylenically unsaturated monomers; and (ii) polymerization to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization cross-linking.

In a separate embodiment, the emulsion polymers are latex polymer particles including a void and comprise from about 0.1 weight percent to about 50 weight percent of latex particles, based on total weight non-volatiles.

The dry polymer compositions improved by the method of this invention has utility in any application where protection from UV radiation is useful. For example, the improved composition may be used on human skin and hair, such as, for example personal care products, including cosmetics, sunscreens, and hair care products; and incorporated in pharmaceuticals applied to skin and hair. In addition, the method of this invention is also useful in further improving the UV radiation-absorption storage stability of compositions for coatings on plant life, plastics, wood, and metal for example in the form of a clear varnish.

According to one embodiment, polymer particles of the invention are included in a personal care composition, the composition comprising at least one UV radiation absorbing agent and dried latex particles prepared from a latex emulsion, the latex particles from the emulsion including a void and having a particle size of from about 100 nm to about 380 nm before drying, wherein the dried latex particles are added to the composition to increase the UV radiation absorption of the composition.

The polymer particles of the present invention are incorporated in personal care, consumer, coating and pharmaceutical compositions and formulations that increase UV radiation absorption of compositions and provide a method for providing storage stability of such compositions. Radiation-absorption compositions include incorporating from 5 to 70%, also incorporating from 10 to 50% and from 20 to 40%, based on total weight non-volatiles in the composition, of latex polymer particles into the composition containing at least one ultraviolet (UV) radiation-absorbing agent; based on total weight of the composition, the level of latex polymer particles is from 0.5 to 10%, including levels of latex particles from 1 to 7% and from 2 to 5%. As used herein, the term "UV radiation" includes both UVA and UVB radiation.

As used herein, the term "non-volatiles" refers to solid or liquid components of the personal care formulation that do not readily evaporate at ambient temperatures due to their vapor pressure (such as polymer particles, UV radiation-absorbing agents and conventional adjuvants).

Accordingly, the invention provides a process for encapsulating one or more active ingredients comprising the steps of: (a) milling one or more hollow sphere polymers; and (b) contacting the milled polymers with one or more active ingredients, including oily substances and hydrophobic materials.

The first step includes milling one or more hollow sphere polymers. Any conventional milling process can be used in accordance with the invention. Alternatively, the polymers can be ground or milled by high shear mixing equipment or the polymers can be fragmented in spray drying equipment, including fluidized bed systems. The milled polymers are contacted with one or more active ingredients, including oily substances and hydrophobic materials. The resulting encapsulated powder particle size is from 1 to 1000 microns, including from 150 to 400 microns. It is also desirable that the slurry particle size distribution is narrow to avoid the presence of dust from very small polymer powder particles and the presence of undesirably large encapsulated particles. The resulting encapsulated powder includes less than 5 weight percent water and forms a free flowing powder. Various methods of drying polymer particle slurries are well known to persons having skill in the art and are described in *Chemical Engineer's Handbook*, $5^{th}$ Ed., Perry and Chilton, Eds., 1973 which relates to the drying of solid-liquid particle dispersions. Conventional drying techniques include but are not limited to fluidized bed drying, rotary drying, spray drying, continuous or batch tray drying, flash drying, and pneumatic conveyor drying. The drying technique usefully employed according to the invention will vary depending on the nature of the polymer and the one or more active ingredients, including oily substances and hydrophobic materials. During the drying step it is useful to control the temperature so that the slurry particles do not fuse among themselves, for example by keep the temperature of the slurry particles below the Tg of the outer shells of the polymer components (also referred to as the hard components). Active ingredients usefully employed in the triggered release system of the invention include oils, oil soluble compounds, water soluble compounds, water insoluble compounds, hydrophobic compounds, flavors, fragrances, perfumes, fabric softeners, bleaches and detergents. Other suitable active ingredients are active ingredients used in cosmetics, cleaners, detergents, personal care products and pharmaceuticals.

Fragrances can be included in the controlled system of the present invention. The fragrances that can be encapsulated in the system of the present invention can be any odoriferous material and can be selected according to the desires of the fragrance creator. In general terms, such fragrance materials are characterized by a vapor pressure below atmospheric pressure at ambient temperatures. The high boiling perfume materials employed herein will most often be solids at ambient temperatures, but also can include high boiling liquids. A wide variety of chemicals are known for perfumery and flavor uses, including materials such as aldehydes, ketones, esters, and the like. More commonly, naturally occurring plant and animal oils and exudates comprising complex mixtures of various chemical components are known for use as fragrances can be used herein. Fragrances useful for the present invention can be a single aroma chemical, relatively simple in their composition, or can comprise highly sophisticated, complex mixtures of natural and synthetic chemical components, all chosen to provide any desired odor.

Suitable fragrance which can be used in the present invention include, for example, high boiling components of woody/earthy bases containing exotic materials such as sandalwood oil, civet, patchouli oil, and the like. The perfumes herein can be of a light, floral fragrance, such as for example, high boiling components of rose extract, violet extract, and the like. The perfumes herein can be formulated to provide desirable fruity odors, such as for example lime, lemon, orange, and the like. The perfume can be any material of appropriate chemical and physical properties which exudes a pleasant or otherwise desirable odor when applied to fabrics. Perfume materials suitable for use in the present invention are described more fully in S. Arctander, Perfume Flavors and Chemicals, Vols. I and II, Aurthor, Montclair, N.J. and the Merck Index, 8th Edition, Merck & Co., Inc. Rahway, N.J., both references being incorporated herein by reference.

As is well known, a perfume normally consists of a mixture of a number of perfumery materials, each of which has a fragrance. The number of perfumery materials in a perfume is typically ten or more. The range of fragrant materials used in perfumery is very wide; the materials come from a variety of chemical classes, but in general are water-insoluble oils. In many instances, the molecular weight of a perfumery material is in excess of 150, but does not exceed 3000.

Perfumes used in the present invention include mixtures of conventional perfumery materials. Suitable perfumes and fragrances include: acetyl cedrene, 4-acetoxy-3-pentyltetrahydropyran, 4-acetyl-6-t-butyl-1,1-dimethylindane, available under the trademark "CELESTOLIDE", 5-acetyl-1,1,2,3,3,6-hexamethylindane, available under the trademark "PHANTOLIDE", 6-acetyl-1-isopropyl-2,3,3, 5-tetramethylindane, available under the trademark "TRASEOLIDE", alpha-n-amylcinnamic aldehyde, amyl salicylate, aubepine, aubepine nitrile, aurantion, 2-t-butylcyclohexyl acetate, 2-t-butylcyclohexanol, 3-(p-t-butylphenyl)propanal, 4-t-butylcyclohexyl acetate, 4-t-butyl-3,5-dinitro-2,6-dimethyl acetophenone, 4-t-butylcyclohexanol, benzoin siam resinoids, benzyl benzoate, benzyl acetate, benzyl propionate, benzyl salicylate, benzyl isoamyl ether, benzyl alcohol, bergamot oil, bornyl acetate, butyl salicylate, carvacrol, cedar atlas oil, cedryl methyl ether, cedryl acetate, cinnamic alcohol, cinnamyl propionate, cis-3-hexenol, cis-3-hexenyl salicylate, citronella oil, citronellol, citronellonitrile, citronellyl acetate, citronellyloxyacetaldehyde, cloveleaf oil, coumarin, 9-decen-1-ol, n-decanal, n-dodecanal, decanol, decyl acetate, diethyl phthalate, dihydromyrcenol, dihydromyrcenyl formate, dihydromyrcenyl acetate, dihydroterpinyl acetate, dimethylbenzyl carbinyl acetate, dimethylbenzylcarbinol, dimethylheptanol, dimethyloctanol, dimyrcetol, diphenyl oxide, ethyl naphthyl ether, ethyl vanillin, ethylene brassylate, eugenol, geraniol, geranium oil, geranonitrile, geranyl nitrile, geranyl acetate, 1,1,2,4,4,7-hexamethyl-6-acetyl-1,2,3,4-tetrahydronaphthalene, available under the trademark "TONALID", 1,3,4,6,7,8-hexahydro-4,6,6,7,8,8-hexamethylcyclopenta-2-benzopyran, available under the trademark "GALAXOLIDE", 2-n-heptylcyclopentanone, 3a,4,5, 6,7,7a-hexahydro-4,7-methano-1(3)H-inden-6-yl-propionate, available under the trademark "FLOROCYCLENE", 3a,4,5,6,7,7a-hexahydro-4,7-methano-1(3)H-inden-6-ylacetate, available under the trademark "JASMACYCLENE", 4-(4'-hydroxy-4'-methylpentyl)-3-cyclohexenecarbaldehyde, alpha-hexylcinammic aldehyde, heliotropin, Hercolyn D, hexyl aldone, hexyl cinnamic aldehyde, hexyl salicylate, hydroxycitronellal, i-nonyl formate, 3-isocamphylcyclohexanol, 4-isopropylcyclohexanol, 4-isopropylcyclohexyl methanol, indole, ionones, irones, isoamyl salicylate, isoborneol, isobornyl acetate, isobutyl salicylate, isobutylbenzoate, isobutylphenyl acetate, isoeugenol, isolongifolanone, isomethyl ionones, isononanol, isononyl acetate, isopulegol, lavandin oil, lemongrass oil, linalool, linalyl acetate, LRG 201, 1-menthol, 2-methyl-3-(p-isopropylphenyl)propanal, 2-methyl-3-(p-t-butylphenyl)propanal, 3-methyl-2-pentyl-cyclopentanone, 3-methyl-5-phenyl-pentanol, alpha and beta methyl naphthyl ketones, methyl ionones, methyl dihydrojasmonate, methyl naphthyl ether, methyl 4-propyl phenyl ether, Mousse de chene Yugo, Musk ambrette, myrtenol, neroli oil, nonanediol-1,3-diacetate, nonanol, nonanolide-1,4, nopol acetate, 1,2,3,4,5,6,7,8-octahydro-2,3,8,8-tetramethyl-2-acetyl-naphthalene, available under the trademark "ISO-E-SUPER", octanol, Oppoponax resinoid, orange oil, p-t-amylcyclohexanone, p-t-butylmethylhydrocinnamic aldehyde, 2-phenylethanol, 2-phenylethyl acetate, 2-phenylpropanol, 3-phenylpropanol, para-menthan-7-ol, para-t-butylphenyl methyl ether, patchouli oil, pelargene, petitgrain oil, phenoxyethyl isobutyrate, phenylacetaldehyde diethyl acetal, phenylacetaldehyde dimethyl acetal, phenylethyl n-butyl ether, phenylethyl isoamyl ether, phenylethylphenyl acetate, pimento leaf oil, rose-d-oxide, Sandalone, styrallyl acetate, 1,1,4,4-tetramethyl-6-acetyl-7-ethyl-1,2,3,4-tetrahydronaphthalene, available under the trademark "VERSALIDE", 3,3,5-trimethyl hexyl acetate, 3,5,5-trimethylcyclohexanol, terpineol, terpinyl acetate, tetrahydrogeraniol, tetrahydrolinalool, tetrahydromuguol, tetrahydromyrcenol, thyme oil, trichloromethylphenylcarbinyl acetate, tricyclodecenyl acetate, tricyclodecenyl propionate, 10-undecen-1-al, gamma undecalactone, 10-undecen-1-ol, undecanol, vanillin, vetiverol, vetiveryl acetate, vetyvert oil, acetate and propionate esters of alcohols in the list above, aromatic nitromusk fragrances indane musk fragrances isochroman musk fragrances macrocyclic ketones, macrolactone musk fragrances and tetralin musk fragrances. Other suitable examples of fragrances and perfumes are described in European Patent Publication EP 1 111 034 A1.

Perfumes frequently include solvents or diluents, for example: ethanol, isopropanol, diethylene glycol monoethyl ether, dipropylene glycol, diethyl phthalate and triethyl citrate.

Perfumes which are used in the invention may, if desired, have deodorant properties as disclosed in U.S. Pat. No. 4,303,679, U.S. Pat. No. 4,663,068 and European Patent Publication EP 0 545 556 A1.

Absorption of perfume can be enhanced by choosing perfumery materials with a hydrophobic character or mixing a hydrophobic oil into the perfume. Suitable examples of hydrophobic oils which can enhance perfume uptake include: dibutylphthalate, alkane mixtures such as isoparaffin and di(C8–C10alkyl) propylene glycol diester.

Water-sensitive, surface active polymers for coating the oil absorbing polymer of the present invention comprise water soluble and water dispersible natural and synthetic polymers and copolymers, starch derivatives, polysaccharides, hydrocolloids, natural gums, proteins, and mixtures thereof.

Examples of synthetic water sensitive polymers which are useful for the invention include polyvinyl pyrrolidone, water soluble celluloses, polyvinyl alcohol, ethylene maleic anhydride copolymer, methylvinyl ether maleic anhydride copolymer, acrylic acid copolymers, anionic polymers of methacrylic acid and methacrylate, cationic polymers with dimethyl-aminoethyl ammonium functional groups, polyethylene oxides, water soluble polyamide or polyester.

Examples of water soluble hydroxyalkyl and carboxyalkyl celluloses include hydroxyethyl and carboxymethyl cellulose, hydroxyethyl and carboxyethyl cellulose, hydroxymethyl and carboxymethyl cellulose, hydroxypropyl carboxymethyl cellulose, hydroxypropyl methyl carboxyethyl cellulose, hydroxypropyl carboxypropyl cellulose, hydroxybutyl carboxymethyl cellulose, and the like. Also useful are alkali metal salts of these carboxyalkyl celluloses, particularly and preferably the sodium and potassium derivatives.

Other suitable hydrophobic materials include but are not limited to for example body oils such as sebum and squalene, proteins, protein containing substances such as food, blood, fat; lipids, fatty acids, waxes, mineral oils, silicone oils, motor oils, crude oils, organic compounds, lipophilic toxins such as PCB, pesticides, insecticides, and herbicides; greases and vegetable oils. The oil-absorbing polymer process has utility in transferring or removing oily substances from surfaces of substrates including for example textiles, fabric, hard surfaces such as ceramics, wood, tile asphalt, cement; human skin, animal skin. Moreover, the oil-absorbing polymer compositions can be usefully combined or formulated with detergents such as those used in the home, industrially or in the environment; cleaners, personal care products such as hair and body washes and cosmetics, medical or pharmaceutical products.

Some embodiments of the invention are described in detail in the following Examples. All ratios, parts and percentages are expressed by weight unless otherwise specified, and all reagents used are of good commercial quality unless otherwise specified. The following abbreviations are used in the Examples:

| | |
|---|---|
| MMA = | Methyl Methacrylate |
| BMA = | Butyl Methacrylate |
| ALMA = | Allyl Methacrylate |
| MAA = | Methacrylic Acid |
| DVB = | Divinylbenzene (80% active, 20% ethylvinylbenzene) |
| Sty = | Styrene |
| SSS = | Sodium Styrene Sulfonate |
| AAEM = | Acetoacetoxyethyl Methacrylate |
| SDBS = | Sodium Dodecylbenzenesulfonate |
| TMPTA = | Trimethylolpropane Triacrylate |
| TEGDA = | Tetraethyleneglycol Diacrylate |
| PBW = | Parts by Weight |
| XL = | Crosslinker |
| NA = | Not Analyzed |
| MFM = | Multifunctional Monomer |

Hollow sphere latex polymer particles and core shell polymer dispersions described in Example 1 were prepared similarly to the method described in U.S. Pat. Nos. 4,427,836 and 6,384,104. Core polymers typically had an average particle diameter of 90 to 150 nm (or 0.09 to 0.15 µl). Polymer #34 was selected as a representative polymer.

EXAMPLES

Example 1

Two grams of a dried hollow sphere polymer (prepared according to the method described in U.S. Pat. No 6,384,104) was milled in an IKA A10 milling device. The milled polymer is contacted with 1 gram of isopropyl palmitate (obtained from Sigma Company) at room temperature for 2 days. A flowable, non-dusting powder was obtained. The powdery is applied to skin and has a powdery feel, with no wetting associated with the encapsulated oily material.

Example 2

Two grams of a dried hollow sphere polymer (prepared according to the method described in U.S. Pat. No 6,384,104) was milled in an IKA A10 milling device. The milled polymer is contacted with 1 gram of isopropyl palmitate (obtained from Sigma Company). The mixture is milled at room temperature for 20 seconds. Milling was stopped to homogenize the powder and oil, then milling of the mixture was repeated. The sequence was repeated 3 times. Milling the polymer and oil mixture reduces the time needed for the polymer to absorb the oil. A flowable, non-dusting powder was obtained. The powdery is applied to skin and has a powdery feel with no wetting associated with the encapsulated oily material.

Example 3

Two grams of a dried hollow sphere polymer (prepared according to the method described in U.S. Pat. No 6,384,104) was milled in an IKA A10 milling device. The milled polymer is contacted with 1 gram of a perfume, Fruity 23™ (obtained from Givaudan Company). The mixture is milled at room temperature for 20 seconds. Milling was stopped to homogenize the powder and perfume, then milling of the mixture was repeated. The sequence was repeated 3 times. Milling the polymer and perfume mixture reduces the time needed for the polymer to absorb the perfume. A flowable, non-dusting powder was obtained. The powdery is applied to skin and has a powdery feel with no wetting associated with the encapsulated perfume.

Example 4

Two grams of a dried hollow sphere polymer (prepared according to the method described in U.S. Pat. No 6,384,104) was milled in an IKA A10 milling device. The milled polymer is contacted with 1 gram of silicone oil, ML200™ (obtained from Dow Corning Company). The mixture is milled at room temperature for 20 seconds. Milling was stopped to homogenize the powder and silicone oil, then milling of the mixture was repeated. The sequence was repeated 3 times. Milling the polymer and silicone oil mixture reduces the time needed for the polymer to absorb the silicone oil. A flowable, non-dusting powder was obtained. The powdery is applied to skin and has a powdery feel with no wetting associated with the encapsulated silicone oil.

Example 5

Two grams of a dried hollow sphere polymer (prepared according to the method described in U.S. Pat. No 6,384,104) was combined with 1 gram of isopropyl palmitate (obtained from Sigma Company) and was milled in an IKA A10 milling device. The mixture is milled at room temperature for 20 seconds. Milling was stopped to homogenize the powder and oil, then milling of the mixture was repeated. The sequence was repeated 3 times. Milling the polymer and oil mixture reduces the time needed for the polymer to absorb the oil. A flowable, non-dusting powder was obtained. The powdery is applied to skin and has a powdery feel with no wetting associated with the encapsulated oily material.

Example 6

Two grams of a dried hollow sphere polymer (prepared according to the method described in U.S. Pat. No 6,384,104) was combined with 1 gram of silicone oil, ML200™ (obtained from Dow Corning Company) and was milled in an IKA A10 milling device. The mixture is milled at room temperature for 20 seconds. Milling was stopped to homogenize the powder and silicone oil, then milling of the mixture was repeated. The sequence was repeated 3 times. Milling the polymer and silicone oil mixture reduces the time needed for the polymer to absorb the silicone oil. A flowable, non-dusting powder was obtained. The powdery is applied to skin and has a powdery feel with no wetting associated with the encapsulated silicone oil.

Example 7

Two grams of a dried hollow sphere polymer (prepared according to the method described in U.S. Pat. No 6,384,104) was combined with 1 gram of a perfume, Fruity 23™ (obtained from Givaudan Company) and was milled in an IKA A10 milling device. The mixture is milled at room temperature for 20 seconds. Milling was stopped to homogenize the powder and perfume, then milling of the mixture was repeated. The sequence was repeated 3 times. Milling the polymer and perfume mixture reduces the time needed for the polymer to absorb the perfume. A flowable, non-dusting powder was obtained. The powdery is applied to skin and has a powdery feel with no wetting associated with the encapsulated perfume.

Example 8

Two grams of a dried hollow sphere polymer (prepared according to the method described in U.S. Pat. No 6,384,104) was combined with 1 gram of dyed isopropyl palmitate (obtained from Sigma Company) and was milled in an IKA A10 milling device. The dye used was Fatty Red™ (obtained from Sigma Company). The mixture is milled at room temperature for 20 seconds. Milling was stopped to homogenize the powder and oil, then milling of the mixture was repeated. The sequence was repeated 3 times. Milling the polymer and oil mixture reduces the time needed for the polymer to absorb the oil. A pink colored flowable, non-dusting powder was obtained, indicating incorporation of the oil and dye in to the hollow sphere polymer. The powdery is applied to skin and has a powdery feel with no wetting associated with the encapsulated oily material or dye.

Example 9

The perfume encapsulated powder of Example 7 was used to prepare a tablet formulation: 10 wt. % perfume encapsulated polymer powder, 58 wt. % lactose, 30 wt. % MCC, 2 wt. % stearate. The ingredients were mixed and tablets were prepared using a Frogeray™ tablet machine. Perfume encapsulated tablets are prepared as a result. The perfume encapsulated tablets float on water.

Example 10

The perfume encapsulated powder of Example 7 was used to prepare a detergent tablet formulation: 10 wt. % perfume encapsulated polymer powder, 58 wt. % detergent additives, 30 wt. % MCC, 2 wt. % stearate. The ingredients were mixed and tablets were prepared using a Frogeray™ tablet machine. Perfume encapsulated detergent tablets are prepared as a result. The perfume encapsulated detergent tablets float on water.

Example 11

As a control, a commercial product EXL-2600™ was employed as a comparative example (obtained from Rohm and Haas Company) which comprised an impact modifier, namely a methylmethacrylate/butadiene/styrene copolymer. The polymer has core shell structure but the core is not empty unlike the hollow sphere polymer described above. Two grams of the polymer was combined with 1 gram of Fruity 23™ (obtained from Givaudan Company) and was milled in an IKA A10 milling device. The mixture is milled at room temperature for 20 seconds. Milling was stopped to homogenize the powder and perfume, then milling of the mixture was repeated. The sequence was repeated 3 times. Milling the polymer and perfume mixture reduces the time needed for the polymer to absorb the perfume. A sticky, fluffy powder was obtained unsuitable for use.

Example 12

As a control, a commercial product BTA-740™ was employed as a comparative example (obtained from Rohm and Haas Company) which comprised an impact modifier, namely a methylmethacrylate/butadiene/styrene copolymer. The polymer has core shell structure but the core is not empty unlike the hollow sphere polymer described above. Two grams of the polymer was combined with 1 gram of Fruity 23™ (obtained from Givaudan Company) and was milled in an IKA A10 milling device. The mixture is milled at room temperature for 20 seconds. Milling was stopped to homogenize the powder and perfume, then milling of the mixture was repeated. The sequence was repeated 3 times. Milling the polymer and perfume mixture reduces the time needed for the polymer to absorb the perfume. A sticky, fluffy powder was obtained unsuitable for use.

I claim:

1. A process for encapsulating one or more oily substances and hydrophobic materials comprising the steps of: (a) milling one or more hollow sphere polymers prepared from latex polymer particles having a particle size from 0.1 to 0.6 microns, and comprising a shell portion prepared by one or more steps selected from: (i) polymerization to incorporate from 4 to 80 percent monomeric units, based on total weight of the shell portion, of one or more polyethylenically unsaturated monomers; and (ii) polymerization to incorporate from 4 to 80 percent monomeric units, based on total weight of the shell portion, of one or more multifunctional monomers having at least one functional group capable of vinyl copolymerization and at least one functional group capable of reaction with a reactive molecule effective to produce post-polymerization cross-linking; (b) contacting the milled polymers with one or more oily substances and hydrophobic materials to form a powder; and (c) incorporating said powder into a cosmetic, sunscreen or hair care product; wherein said one or more oily substances and hydrophobic materials comprise at least one fragrance.

2. The process of claim 1 in which said at least one fragrance has a molecular weight in excess of 150, but no more than 3,000.

3. The process of claim 2 in which said at least one fragrance is an aldehyde, ketone or ester.

4. The process of claim 3 in which said at least one fragrance is an ester.

5. The process of claim 1 in which said at least one fragrance is a naturally occurring plant or animal oil.

* * * * *